US00PP35759P2

(12) United States Plant Patent
Hansen

(10) Patent No.: US PP35,759 P2
(45) Date of Patent: Apr. 16, 2024

(54) ***AGASTACHE* PLANT NAMED 'BLUE BAYOU'**

(50) Latin Name: ***Agastache* hybrid**
Varietal Denomination: Blue Bayou

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/803,931

(22) Filed: Jan. 26, 2023

(51) Int. Cl.
*A01H 5/02* (2018.01)
*A01H 6/50* (2018.01)

(52) U.S. Cl.
USPC ..... Plt./399
CPC ..... *A01H 6/50* (2018.05)

(58) Field of Classification Search
USPC ..... Plt./399
CPC ..... A01H 5/02
See application file for complete search history.

*Primary Examiner* — Kent L Bell

(57) ABSTRACT

A new and unique cultivar of hyssop, *Agastache* plant named 'Blue Bayou' with medium-sized, dense, mounded, well-branched, upright, winter-hardy habit and dark green foliage color with wine-colored underside as emerging. The new plant is freely-flowering with flowers of dark purple coloration beginning in early summer and continuing into fall with densely branched panicles. The new plant has excellent vigor, is resistant to deer and rabbits, and is useful in the landscape and as a cut flower.

1 Drawing Sheet

Botanical denomination: *Agastache* hybrid.
Variety designation: 'Blue Bayou'.

STATEMENT REGARDING PRIOR DISCLOSURES UNDER 37 CFR 1.77(B)(6)

The first non-enabling information of the claimed plant was made by Walters Gardens, Inc. on Feb. 1, 2022, in the form of a website brief description and photograph followed by a short description. The first enabling disclosure of a sale of the claimed plant was on Dec. 12, 2022, by Walters Gardens, Inc to Dozer Dog Farms, Inc. Walters Gardens, Inc. obtained the new plant and information about the new plant directly from the inventor. No plants of *Agastache* 'Blue Bayou' have been sold, in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct hyssop plant or anise hyssop plant from the genus *Agastache* and given the cultivar name 'Blue Bayou'. The new plant was the result of a single seedling selection from a cross-pollination on Jul. 15, 2015, by the inventor of 'Blue Boa' U.S. Plant Pat. No. 24,050 as the female or seed parent and the proprietary, unreleased, hybrid, clone *Agastache* HK10-02-09 (not patented) as the male or pollen parent. The seeds from the cross were collected in the late summer of 2015. The individually selected seedling was eventually given the breeder code 15-10-1 after being first isolated from trials at a wholesale perennial nursery in Zeeland, MI during the summer of 2018. It was selected for the final introduction in the summer of 2020.

*Agastache* 'Blue Bayou' has been asexually propagated since 2017 at the same nursery in Zeeland, MI using basal shoot cutting procedures and found to reproduce plants that are identical and exhibit all the characteristics of the original plant in successive generations of asexual propagation.

The new plant, *Agastache* 'Blue Bayou', has not been observed under all possible environments. The phenotype may vary slightly with different environmental conditions, such as temperature, light, fertility, moisture, and maturity levels, but without any change in the genotype.

In comparison, the female parent is taller and more upright in habit, has longer inflorescences with less branching, and the flower color is more mauve-blue. The male parent is mounded with apricot-colored flowers.

The nearest comparison varieties known to the inventor are: 'Blue Boa' U.S. Plant Pat. No. 24,050, 'Blue Fortune' (not patented), 'Little Adder' U.S. Plant Pat. No. 26,514, and 'TNAGAPDB' U.S. Plant Pat. No. 28,950.

'Blue Fortune' has a taller habit, with less branching, and longer inflorescences with a softer shade of blue flowers. 'Little Adder' has a shorter habit and the flowers have smaller lobes and are more violet-colored. 'TNAGAPDB' has lighter-colored flowers of a more purplish hue.

The new plant *Agastache* 'Blue Bayou' is distinct from the parents and all other anise hyssop plant known to the inventor in the following combined traits:

1. Medium-sized, dense, well-branched, upright, habit;
2. Freely flowering with flowers of dark-purple coloration in dense verticils;
3. Long bloom time with effectiveness extended by heavily compound-branched panicles;
4. Excellent vigor, good winter hardiness, and resistance to deer and rabbit;

BRIEF DESCRIPTION OF THE DRAWINGS

The drawings are of two-year-old plants in mid-season flower in a trial block at a nursery in Zeeland, Michigan and demonstrate the overall appearance of the new plant, including its unique traits. The colors are as accurate as reasonably possible with color reproductions. Ambient light spectrum, temperature, source, and direction may cause the appearance of minor variations in color.

DETAILED PLANT DESCRIPTION

Figure 1:
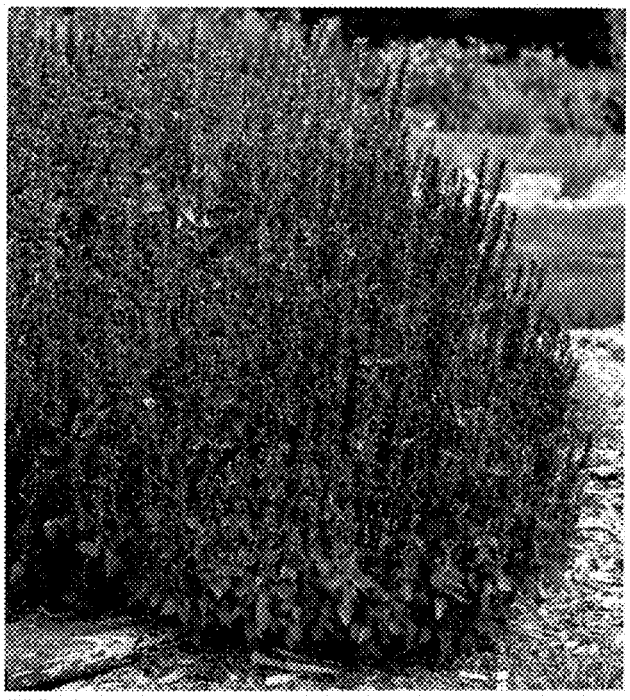
FIG. 1 shows a side view of two-year-old plants in mid-season flower in a trial block at a nursery in Zeeland, Michigan.
Figure 2:
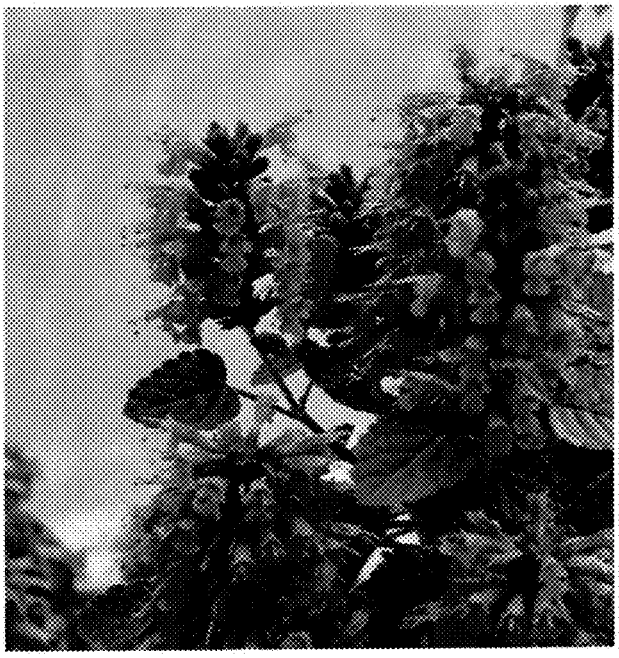
FIG. 2 shows a close-up of a peduncle branch with flowers, buds, and calyxes.

The following is a detailed description of the new *Agastache* cultivar 'Blue Bayou' based on observations of two-year-old specimens grown in a container in a partially shaded greenhouse and in a display garden at a wholesale perennial nursery in Zeeland, MI. Color descriptions are from the 2015 edition of The Royal Horticultural Society Colour Chart except where common dictionary terms are used.

Plant habit: Multi-stemmed herbaceous perennial, rounded, heavily branched;

Plant size: Without growth retardants or pinching — to about 45 cm tall and 44 cm across;

Roots: Fibrous, well-branched; to about 2 mm diameter near base; color light tan nearest RHS 165D depending on soil type;

Stem: Quadrangular; fistulous; stiff; wiry; finely pubescent; to about 4 mm across at base and 45 cm tall with flowering starting about 10 cm above soil; 10 internodes below branched peduncle; internodes average about 2.7 cm long; about eight to ten stems per plant;

Primary branches: Quadrangular; opposite; about 8 to 10 per plant; to about 30 cm long and about 2.5 mm diameter at base;

Secondary branches: Quadrangular; opposite; 4 to 6 per primary branch; to about 20 cm long and 2.5 mm diameter at base;

Stem, primary branch, and secondary branch color: Proximal and distal portions nearest RHS 146B, with light to moderate blush to nearly solid color of nearest RHS N186C in regions exposed to higher light intensities; nodes nearest RHS 146B;

Leaf: Simple; opposite; ovate, base cordate to rounded; apex acute; margin crenate with five to eight rounded teeth per side; adaxial and abaxial surfaces micro-puberulent, initially slightly lustrous adaxial and becoming matte, and matte abaxial;

Leaf size: To about 35 mm long and 25 mm wide near base, decreasing distally;

Leaf venation: Reticulate; glabrous and slightly impressed adaxial, micro-puberulent and costate abaxial;

Leaf color: Young expanding adaxial between RHS 137A and RHS 137B, abaxial nearest RHS N77A with faint undertone of nearest RHS 146B; mature adaxial nearest RHS NN137B, mature abaxial nearest RHS 147B;

Vein color: Mature adaxial nearest RHS 151A, mature abaxial main proximal veins nearest RHS 148C and distal veins nearest RHS 137B; expanding adaxial veins proximal main veins nearest RHS N163C and distal veins nearest RHS 137B; expanding abaxial main veins nearest RHS 148C and distal veins nearest RHS N77A;

Leaf fragrance: Moderately herbal, minty;

Petiole: Concavo-convex; micro-puberulent adaxial and abaxial; to 19 mm long and 2 mm across, average 14 mm long and 1.5 mm;

Petiole color: Adaxial nearest RHS 148C with a light blush of nearest RHS N77A; abaxial nearest RHS 147C with a faint blush of nearest RHS N77A;

Inflorescence: In densely branched panicle with short branches or whorls in axils; 8 to 60 flowers on two short branchlets per node; up to 16 nodes per main stem, and up to 800 flowers per main stem; flowering portion about 20 cm long and about 4 cm across; total flowering portion about 35 cm long and about 11 cm across; each stem flowering for about 5 weeks;

Bloom period: Early July through early fall in Zeeland, Michigan;

Peduncle: Average about 30 cm tall and about 3 mm at base of flowers; puberulent; aspect upwardly;

Peduncle color: Nearest RHS 146B;

Pedicel: Cylindrical; short; glabrous; matte; attitude mostly upright; to about 2 mm long and 0.5 mm diameter; color nearest RHS 148C;

Flower: Perfect; complete; zygomorphic; sympetalous; bilabiate, with five sympetalous petals forming an upper lip 2-lobed and lower lip 3-lobed; attitude outwardly to slightly upwardly;

Flower size: About 29 mm long to exerted stamens, about 11 mm tall and 7 mm across; corolla to about 25 mm long, 6 mm tall, and 7 mm across, tube about 3 mm diameter at fusion of two lips; corolla 13 mm long and 7 mm tall and 4 mm wide at apex; aspect mostly outwardly;

Flower period: Individual flowers open for about 3 days; individual main panicle lasting for about 3 weeks extending to 5 weeks with branching; and entire plant flowering from early summer to fall if deadheaded;

Bud one day prior to opening: Arcuate; clavate; about 10 mm long, 3.5 mm tall and 3 mm wide just before the apex and 1.5 mm wide at base;

Bud color: Exposed petals nearest RHS 79B; calyx variable, base between RHS 195D and RHS 196D, distally nearest RHS 148A with veins and variable blushing of nearest RHS N77A;

Petals: Glabrous adaxial except puberulent at fusion of lower labium; micro-puberulent abaxial; upper and lower petals proximally fused forming tube in the basal 8 mm long and 3 mm diameter toward fusion of the two petals; both petals matte in both adaxial and abaxial;

Upper labium: 2-lobed; about 13 mm long and 3 mm across toward apex; lobes centrally cleft about 1 mm deep; lobe apices rounded; margin entire;

Lower labium: 3-lobed; about 12 mm long, center lobe to 3 mm long and 4 mm wide, reflexed to a 90° angle in distal 3 mm, apex rounded with crenate margin; two side lobes to 2 mm long and 2 mm wide; reflexed to a 90° angle in distal 3 mm; center lobe comprising two side lobes reflexed to nearly a 90° angle in distal 2 mm, with rounded apex and entire margin;

Petal color: Adaxial and abaxial upper and lower labium upon first opening nearest RHS 86B; just before dropping adaxial and abaxial upper and lower labium between RHS 83B and RHS 86B; adaxial corolla tube basal throat portion nearest RHS N155C and throat distally nearest RHS 86B; abaxial corolla tube basal throat portion nearest RHS N77C;

Calyx: Campanulate; about 6 mm long and diameter about 3 mm at apex;

Sepals: Five; linear; acute apices; entire margin; to about 6 mm long and 1 mm wide at fusion, fused into tube in basal 5 mm; micro-puberulent outside and glabrous inside; matte both surfaces;

Sepal color: Adaxial proximally between RHS 146D and RHS 145A, distally nearest RHS 146D heavily blushed with nearest RHS 187B; adaxial proximally between RHS 146D and RHS 145A, distally nearest RHS 146D lightly blushed with nearest RHS 187B, veins nearest RHS 187B;

Gynoecium: Single; to 16 mm long; exerted;

*Style*.—One; about 14 mm long and about 0.3 mm diameter; terete; glabrous; slightly arcuate; lustrous; color distally nearest RHS N82D, proximal 3 mm nearest RHS NN155D.

*Stigma*.—Bifid and reflex; each segment about 1 mm long and about 0.2 mm diameter; apices tapering to a point; color nearest RHS 79B.

*Ovary*.—Superior; globose; about 1 mm diameter; color nearest RHS 145A.

Androecium: In two sets of two, exerted;

*Filaments*.—Two longer and two shorter; paired and exerted; adnate to the corolla; longer pair to 18 mm long and adnate in the basal 11 mm and free in the proximal 7 mm; shorter pair to 15 mm long and adnate in the basal 8 mm and free in the proximal 7 mm; color both sets nearest RHS N82D.

*Anthers*.—Dorsifixed; versatile; longitudinal; to about 1 mm long and about 0.5 mm across; color between RHS 83A and RHS N79B.

*Pollen*.—Abundant; color nearest RHS 155C.

Fragrance: None detected;

Fruit: Two carpels;

Seed: Nutlet; typically, one to two per naturally pollinated flower; globose; about 1 mm diameter;

Seed color: Between RHS 200A and RHS 200B;

Resistance: 'Blue Bayou' is resistant to Downy Mildew (*Peronospora*) and shows no susceptibility to *Odocoileus, Sylvilagus*, or *Oryctolagus* browsing but has not been tested or shown resistance to other pests and diseases common to *Agastache*.

Hardiness: The new plant has survived USDA hardiness zones 5 to 9 but has not been tested yet beyond these temperatures.

The invention claimed is:

1. A new and distinct cultivar of *Agastache* plant named 'Blue Bayou' as herein described and illustrated.

* * * * *